United States Patent
Song et al.

(10) Patent No.: US 10,737,158 B2
(45) Date of Patent: Aug. 11, 2020

(54) METHOD AND DEVICE FOR RECOGNIZING MOVEMENT OF TENNIS RACKET

(71) Applicant: SHENZHEN COOLLANG CLOUD COMPUTING CO., LTD, Shenzhen, Guangdong Province (CN)

(72) Inventors: Zhicong Song, Shenzhen (CN); Rongqing Li, Shenzhen (CN); Qicai Zhong, Shenzhen (CN)

(73) Assignee: ShenZhen Coollang Cloud Computing Co., LTD, Shenzhen, Guangdong Province (CN)

( * ) Notice: Subject to any disclaimer, the term of this patent is extended or adjusted under 35 U.S.C. 154(b) by 105 days.

(21) Appl. No.: 15/817,355

(22) Filed: Nov. 20, 2017

(65) Prior Publication Data
US 2018/0140917 A1    May 24, 2018

(30) Foreign Application Priority Data
Nov. 21, 2016    (CN) .......................... 2016 1 1026322

(51) Int. Cl.
*A63B 60/46*    (2015.01)
*A63B 24/00*    (2006.01)
(Continued)

(52) U.S. Cl.
CPC .......... *A63B 60/46* (2015.10); *A63B 24/0006* (2013.01); *A63B 69/38* (2013.01);
(Continued)

(58) Field of Classification Search
CPC ............ A63B 2225/50; A63B 2220/40; A63B 24/0003; A63B 69/38; A63B 2220/53; A63B 49/00; A63B 60/46
See application file for complete search history.

(56) References Cited

U.S. PATENT DOCUMENTS

| | | | |
|---|---|---|---|
| 8,109,816 B1 * | 2/2012 | Grober | A63B 69/3632 463/3 |
| 2010/0130298 A1 * | 5/2010 | Dugan | A63B 69/3623 473/223 |

(Continued)

FOREIGN PATENT DOCUMENTS

| | | |
|---|---|---|
| CN | 101504834 A | 8/2009 |
| CN | 103076884 A | 5/2013 |

(Continued)

OTHER PUBLICATIONS

The CN1OA dated Mar. 4, 2019 by the CNIPA.
The ISR issued Jun. 1, 2017 by the WIPO.

*Primary Examiner* — William H McCulloch, Jr.
*Assistant Examiner* — Ankit B Doshi
(74) *Attorney, Agent, or Firm* — Yunling Ren

(57) ABSTRACT

The present disclosure relates to a method and device for recognizing movement of a tennis racket, the method includes: collecting swing data of the tennis racket; extracting an data segment of an effective swing from the swing data of the tennis racket according to an effective ball hitting position; performing matching calculation between the data segment of the effective swing and preset template data, the preset template data corresponding to types of tennis racket movements; and acquiring a recognition result of the movement of tennis racket according to a result of the matching calculation. The method and device for recognizing movement of the tennis racket can improve the accuracy of the process of matching, avoid miscalculations of types of the swing movement of the tennis racket.

8 Claims, 11 Drawing Sheets

(51) Int. Cl.
    *A63B 69/38*     (2006.01)
    *A63B 49/00*     (2015.01)
    *G16H 20/30*     (2018.01)
    *G16H 40/63*     (2018.01)
    *A63B 102/02*    (2015.01)

(52) U.S. Cl.
    CPC ............ *G16H 20/30* (2018.01); *G16H 40/63* (2018.01); *A63B 49/00* (2013.01); *A63B 2024/0012* (2013.01); *A63B 2102/02* (2015.10); *A63B 2220/56* (2013.01); *A63B 2220/72* (2013.01); *A63B 2220/833* (2013.01); *A63B 2220/89* (2013.01); *A63B 2225/50* (2013.01)

(56) References Cited

U.S. PATENT DOCUMENTS

2013/0203518 A1\* 8/2013 Hatton ................. A63B 53/047
                                                      473/223
2015/0057112 A1\* 2/2015 Sak .................... A63B 24/0003
                                                      473/461

FOREIGN PATENT DOCUMENTS

| | | |
|---|---|---|
| CN | 103412886 A | 11/2013 |
| CN | 103542843 A | 1/2014 |
| CN | 105184325 A | 12/2015 |
| CN | 105617638 A | 6/2016 |
| CN | 105786182 A | 7/2016 |
| JP | 2004201792 A | 7/2004 |

\* cited by examiner

METHOD AND DEVICE FOR RECOGNIZING MOVEMENT OF TENNIS RACKET

CROSS-REFERENCE TO RELATED APPLICATIONS

The present application claims priority to Chinese Patent Application No. 201611026322.9, filed on Nov. 21, 2016, the entire contents of which are incorporated herein by reference.

TECHNICAL FIELD

The present disclosure generally relates to the field of computer application technology, and more particularly, to a method and device for recognizing movement of tennis racket.

BACKGROUND

With the development of information and intelligence technology, there is more and more research on intelligent recognizing of the sport of tennis. Existing technology for tracking and recognizing the swing movement of tennis racket mainly includes a recognizing technology based on image video and recognizing technology based on sensors.

The recognizing technology based on image video mainly uses a high-speed camera to capture a mark provided on the tennis ball, thereby obtaining movement information of the tennis racket, and this method depends on analyzing and processing the image and the video. The recognizing technology based on sensors mainly uses an accelerometer sensor, a gyroscope sensor or the like to measure parameter information such as the special moving path, the speed and the rotational angle of various types of tennis, and further analyzing the parameters to recognize the racket swing.

However, High-speed cameras are necessary in recognizing technology based on image video, and the high-speed camera is expensive and inconvenient to carry. Accordingly, the recognizing technology based on image video only applies to professional training scenarios, and has high requirements on hardware platform and processing capability, which limits its scope of application.

On the other hand, although there are little limitations on the cost and application of the recognizing technology based on sensors, it is difficult to extract characteristic values of various types of movements due to the fact that the information such as accelerated speed and rotational angle or the like, which serve as the characteristic value, among various racket swing movements are similar, resulting in relatively high complexity and low distinguishability, and in turn resulting in too many errors in recognition result of the movement of tennis racket.

SUMMARY

In order to solve the problem in related technologies, the present disclosure provides a method and device for recognizing movement of a tennis racket.

According to a first aspect of embodiments of the present disclosure, there is provided a method for recognizing movement of a tennis racket, comprising:

collecting swing data of the tennis racket;

extracting an data segment of an effective swing from the swing data of the tennis racket according to an effective ball hitting position;

performing matching calculation between the data segment of the effective swing and preset template data, the preset template data corresponding to types of tennis racket movements; and acquiring a recognition result of the movement of tennis racket according to a result of the matching calculation.

According to a second aspect of the embodiments of the present disclosure, there is provided a device for recognizing movement of a tennis racket, comprising:

a collector, configured to collect swing data of the tennis racket;

an extractor, configured to extract an data segment of an effective swing from the swing data of the tennis racket according to an effective ball hitting position a matching calculator, configured to perform matching calculation between the data segment of the effective swing and preset template data, the preset template data corresponding to types of tennis racket movements; and a recognizer, configured to acquire a recognition result of the movement of tennis racket according to a result of the matching calculation.

According to a third aspect of the embodiments of the present disclosure, there is provided a computer program product which, when being executed on a processor of a tracking apparatus, performs a method according to the above aspect.

According to a fourthly aspect of the embodiments of the present disclosure, there is provided a device for recognizing tennis movement, comprising:

a processor; and a memory for storing instructions executable by the processor;

wherein the processor is configured to perform a method according to the above aspect.

It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of devices and methods consistent with aspects related to the invention as recited in the appended claims.

In one embodiment, the implementation environment of the present disclosure may include an intelligent hardware and a module of recognizing movement of tennis racket within the intelligent hardware. The intelligent hardware has an independent operating system and the space of running, it can be equipped with software and the third-party software, for example, the intelligent hardware may be various intelligent systems processing hardware or the like. The module of recognizing movement of tennis racket is a hardware module for recognizing types of movements of tennis racket.

Figure 1:
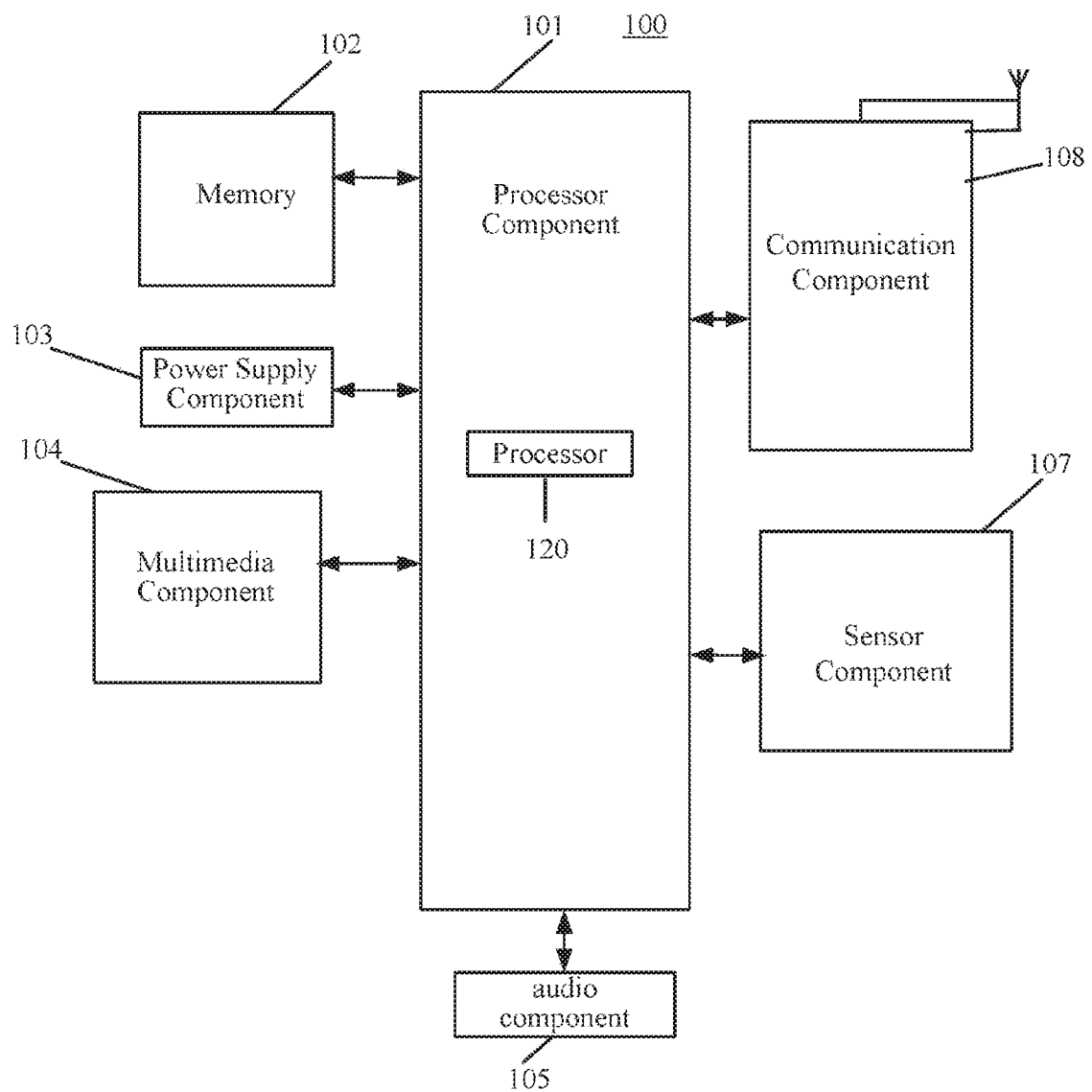
FIG. 1 is a structural block diagram of a device for recognizing tennis racket movement according to an exemplary embodiment.

FIG. 1 is a structural block diagram of a device 100 for recognizing tennis racket movement according to an exemplary embodiment. The device 100 is applicable in a computer device in the above implementation environment.

Referring to FIG. 1, the device 100 may include one or more of the following components: a processing component 101, a memory 102, a power supply component 103, a multimedia component 104, an audio component 105, a sensor component 107, and a communication component 108.

The processing component 101 typically controls overall operations of the device 100, such as operations associated with display, phone call, data communications, camera operations, and recording operations or the like. The processing component 101 may include one or more component to execute instructions to perform all or part of the steps in the above described methods. Moreover, the processing component 101 may include one or more modules which facilitate the interaction between the processing component 101 and other components. For instance, the processing component 101 may include a multimedia module to facilitate the interaction between the multimedia component 104 and the processing component 101.

The memory 102 is configured to store various types of data to support the operation of the device 100. Examples of such data include instructions for any applications or methods operated on the device 100. The memory 102 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk. The memory 102 may include one or more modules, one or more modules are configured to be executed by one or more processors 109 to complete all or part of the steps in either FIG. 2, FIG. 3, FIG. 4, FIG. 5 or FIG. 6.

The power supply component 103 provides power to various components of the device 100. The power supply component 103 may include a power management system, one or more power sources, and any other components associated with the generation, management, and distribution of power in the device 100.

The multimedia component 104 includes a screen that provides an output interface between the device and the user. In some embodiments, the screen may include Liquid Crystal Display (LCD) and Touch Panel (TP). If the screen includes a touch panel, the screen may be implemented as a touch screen to receive input signals from the user. Touch panel includes one or more touch sensors to sense touches, swipes, and gestures on the touch panel. Touch sensors can sense not only the boundaries of touch or swipe motions, but also the duration and pressure associated with touch or swipe operations.

The audio component 105 is configured to output and/or input audio signals. For instance, the audio component may include a microphone, when the device 100 is in operating mode, such as call mode, recording mode and voice recognition mode, the microphone is configure to receive external audio signal. The received audio signal may be further stored in the memory 102 or transmitted via the communication component 108. In some embodiments, the audio component 105 also includes a speaker that outputs the audio signal.

The sensor component 107 includes one or more sensors to provide status assessments of various aspects of the device 100. For instance, the sensor component 107 may detect device 100 on/off status, the relative positioning of components. The sensor component 107 can also detect a change in the position and temperature of a component of the device or device. In some embodiments, the sensor component 107 also includes magnetic sensor, pressure sensor or temperature sensor.

The communication component 108 is configured to facilitate communication, wired or wirelessly, between the device 100 and other devices. The device 100 can access a wireless network based on a communication standard, such as WiFi, 2G, or 3G, or a combination thereof. In one exemplary embodiment, the communication component 108 receives a broadcast signal or broadcast associated information from an external broadcast management system via a broadcast channel. In one exemplary embodiment, the communication component 108 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the device 100 may be implemented with one or more application specific integrated circuit (ASIC), digital signal processor (DSP), digital signal processing device (DSPD), programmable logic device (PLD), field programmable gate array (FPGA), controllers, micro-controller, microprocessors or other electronic component, for performing the following described methods.

Figure 2:
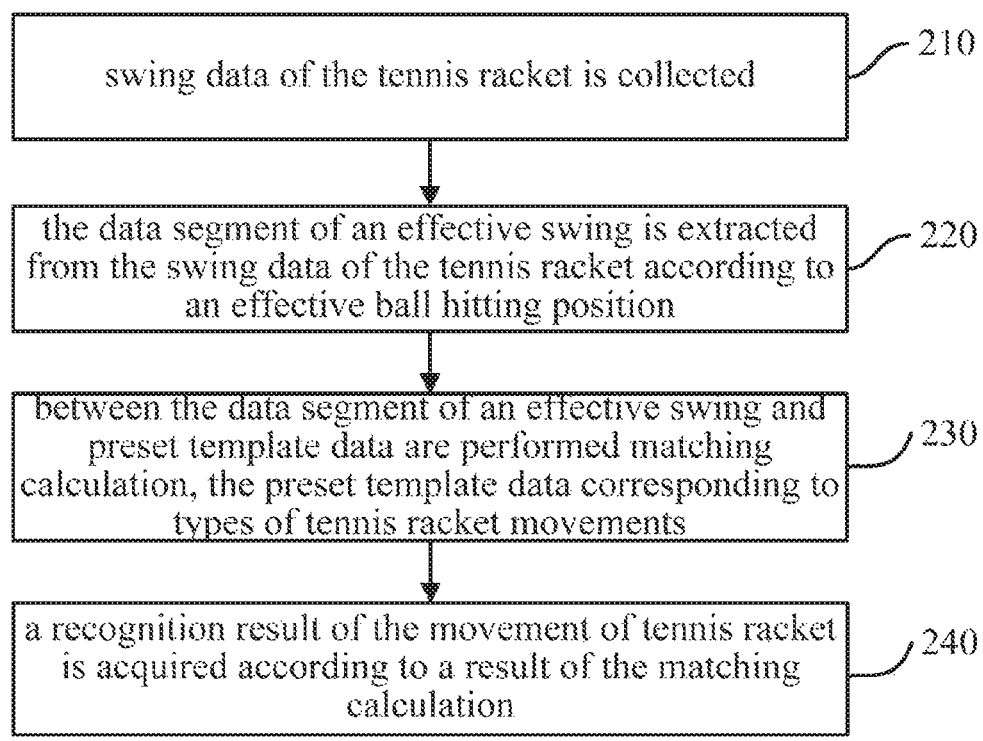
FIG. 2 is a flow chart showing a method for recognizing movement of a tennis racket according to an exemplary embodiment.

FIG. 2 is a flow chart showing a method for recognizing movement of a tennis racket according to an exemplary embodiment. The method is applicable to the tracking apparatus, the tracking apparatus is adapted to a tennis racket, and the method may include following steps as shown in FIG. 2.

In Step 210, swing data of the tennis racket is collected.

The swing data of the tennis racket is continuous collected during a process of swing of the tennis racket. The collected swing data of the tennis racket reflects the parameters corresponding to the swing movement of racket tennis, such as the moving path, speed, rotational angle, accelerated speed or the like. The swing data of the tennis racket is continuously collected throughout the swing of the tennis racket, until the end of the swing movement.

According to an embodiment, the swing data of the tennis racket is collected at a preset sampling frequency throughout the swing of the tennis racket. In a specific exemplary embodiment, the collection of the swing data is performed at a preset sampling frequency for example 100 HZ.

In one embodiment, the swing data of the tennis racket may contain the three-axis gyroscope data, the three-axis accelerated data, and the three-axis resultant force components data which is generated by combination thereof, and the output format of one frame swing data of the tennis racket includes a matrix of a six-axis characteristic vector. During a process for recognizing types of movements of the tennis racket through the swing data, the swing data adopted contain at least one of the three-axis gyroscope data, the three-axis accelerated data, and the components data, or combination thereof.

In Step 220, the data segment of an effective swing is extracted from the swing data of the tennis racket according to an effective ball hitting position.

Because the swing data of the tennis racket may correspond to the whole swing process, and the normal swing movement contains the effective motion and the ineffective motion, types of movements mainly show up in the effective motion.

In one embodiment, the effective motion includes the effective swing motion and the effective ball hitting motion. The ineffective motion includes all kind of wrong swing and ineffective ball hitting motion, the impurity swing motion. The impurity swing motion includes all kind of the un-intentional action such as the empty action, the knocking action of the tennis racket, and the action of hitting the tennis racket against the ground, the action of disassembling sensor in the tennis racket or the like.

In view of the above, the effective motion is only a part of the whole swing process. The effective motion does not occupy the whole swing process, correspondingly, need to segmentation process the swing data of tennis racket, extracting is follow. Extracting the data segment corresponding to the effective motion. That is extracting the swing data segment of an effective swing.

Implementation of extracting the data segment of an effective swing depends on detecting an effective ball hitting position. The effective ball hitting position is a collecting spot during the tennis racket hitting a tennis ball.

In particular, according to the swing data of the tennis racket in the effective ball hitting position, based on the effective ball hitting position, selecting collecting spots within a continuous time range that contains the effective ball hitting position, in these collecting spots the collected swing data of the tennis racket form the data segment of an effective swing.

Because types of movements mainly show up in the stage of tennis ball hitting, so through the effective ball hitting position extracting the data segment of an effective swing, it can be improving the accuracy in the recognition results of the tennis racket swing movements.

In Step 230, between the data segment of an effective swing and preset template data are performed matching calculation, the preset template data corresponding to types of tennis racket movements.

Pre-configuring swing data of each type of movement in tennis racket swing movement as template data, the template data of different type of movement is different in tennis racket swing movement; different template data has their type of movement.

For different types of movements and the un-intentional action, respectively extracting the swing data of the tennis racket, the preset extracted swing data of the tennis racket is stored as the template data. The Template data is different among various of types of tennis racket movement. Different template data has their type of movement.

To the data segment of an effective swing and template data, matching calculation is carried out. For the data segment of an effective swing, similarity matching is performed on all of the template data to obtain similarity measure.

In Step 240, a recognition result of the movement of tennis racket is acquired according to a result of the matching calculation.

According to similarity measure of the data segment of the effective swing and the template data, selecting the template data corresponding the highest similarity matching the data segment of the effective swing, and then acquiring the type of the movement in tennis racket swing movement.

For example, presetting the template data A, the template data B and the template data C. The template data A is corresponding to the type X of the movement, the template data B is corresponding to the type Y of the movement, the template data C is corresponding to the type Z of the movement. For the data segment of an effective swing, respectively calculating similarity measure with the template data A, the template data B and the template data C, and thereby the calculated similarity measure with the template data A is 90, the calculated similarity measure with the template data B is 30, the calculated similarity measure with the template B is 70. The type X of the movement corresponding to template data A is the type of the movement for the data segment of an effective swing.

In the above technical solution, firstly through an effective ball hitting position, extracting a data segment of an effective swing from the swing data of the tennis racket; then, performing matching calculation between the data segment of the effective swing and preset template data; and finally according to similarity measure between the data segment of the effective swing and template data, recognizing the type of movement corresponding template data of the highest similarity measure as the type of the movement of the racket tennis. During a process of recognizing movement, through the effective ball hitting position, extracting the data segment of the effective swing from the swing data of the tennis racket, filtering the ineffective motion to eliminate disturb for recognizing types of movements, and thereby the accuracy of a process of matching and recognizing movement of the tennis racket can be improved, avoid miscalculations.

The technical solutions provided by the embodiments of the present disclosure may have the following beneficial effects.

When recognizing types of movements of the tennis racket, the technical solution collects the swing data of the tennis racket, extracts the data segment of the effective swing from the swing data of the tennis racket according to the effective ball hitting position, performs matching calculation between the swing data segment of the effective swing and template data, wherein the tem plate data corresponds to types of tennis racket movements, and obtains the corresponding recognition results of tennis racket movement according to the result of the matching calculation. During the process of recognizing movement, by extracting the swing data segment of the effective swing according to the effective ball hitting position, it is possible to avoid interferences from the ineffective motions. Further, the type of the racket swing movement is recognized according to the matching between the swing data segment of the effective swing and the template data, thereby ensuring the matching accuracy, improving the accuracy of recognizing types of movements, and avoiding misjudgment of the types of the swing movement of the tennis racket.

Figure 3:
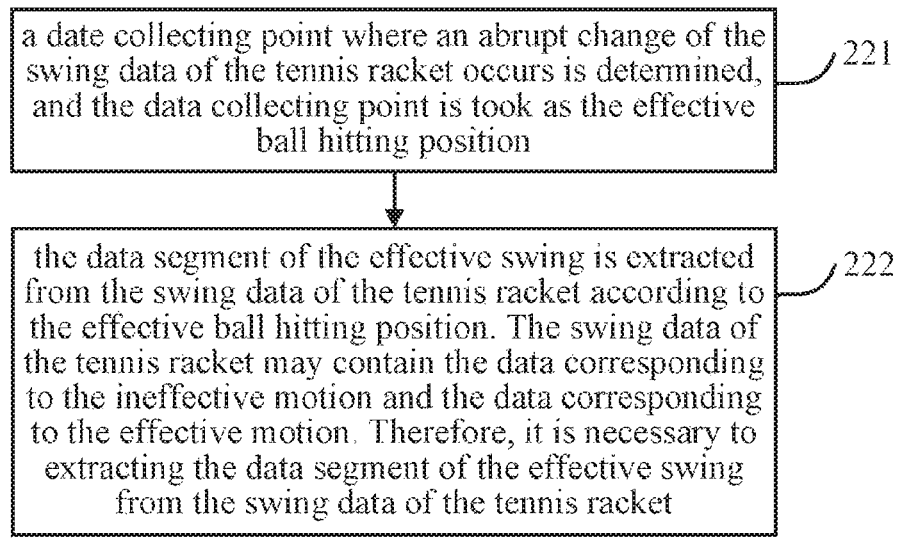
FIG. 3 is a flow chart illustrating a method for the data segment of an effective swing is extracted from the swing data of the tennis racket according to an effective ball hitting position according to another embodiment as shown in FIG. 2.

FIG. 3 is a flow chart illustrating a method for the data segment of an effective swing is extracted from the swing data of the tennis racket according to an effective ball hitting position according to another embodiment as shown in FIG. 2. In one embodiment, as shown in FIG. 3, Step 220 include the following steps.

In Step 221, a date collecting point where an abrupt change of the swing data of the tennis racket occurs is determined, and the data collecting point is took as the effective ball hitting position.

Comparing with other data collecting point, the determined data collecting point is an abrupt change of the swing data of the tennis racket occurs.

During a process of normal swing of the tennis racket, the swing data of the tennis racket generally has a smooth variation. When a tennis ball is hit by the tennis racket, the movement path of the tennis racket instantaneous happen great variation, and result in the swing data of the tennis racket generating an abrupt change. Therefore, by determining the data collecting point where an abrupt change of the swing data of the tennis racket occurs as the effective ball hitting position, it can be improve the accurately in data extracting.

In Step 222, the data segment of the effective swing is extracted from the swing data of the tennis racket according to the effective ball hitting position. The swing data of the tennis racket may contain the data corresponding to the ineffective motion and the data corresponding to the effective motion. Therefore, it is necessary to extracting the data segment of the effective swing from the swing data of the tennis racket.

Various types of the effective motions mainly focus on the effective ball hitting position. Therefore, for the data segment of the effective swing which can be embodying the type of the movement of the tennis racket, the data segment of the effective swing is the swing data of the racket tennis including the effective ball hitting position for a period of time.

In one embodiment, respectively extracting the data collecting point before and after based on the effective ball hitting position, to obtain the data segment of an effective swing; the length of the data segment of the effective swing is 2W. In other word, the number of the extracted data collecting point is 2 w.

In one embodiment, depending on the number of extracting forward and backward the data collecting point from the effective ball hitting position, extracting the data collecting point to obtain the data segment of an effective swing. For example, the effective ball hitting position is the ith data collecting point in the swing data of the tennis racket. The number of extracting forward and backward the data collecting point from the effective ball hitting position are 11 and 12. If 11≥w, and 12≥w, the data segment of an effective swing is within the range of i−w~i+w; if 11≥w, and 12<w, the data segment of an effective swing is within the range of i−w~i+12; if 11<w and 12≥w, the data segment of an effective swing is within the range of i−11~i+w; if 11<w, and 12<w, the data segment of an effective swing is within the range of i−11~i+12.

In a specific exemplary embodiment, w is configured to 50.

Figure 4:
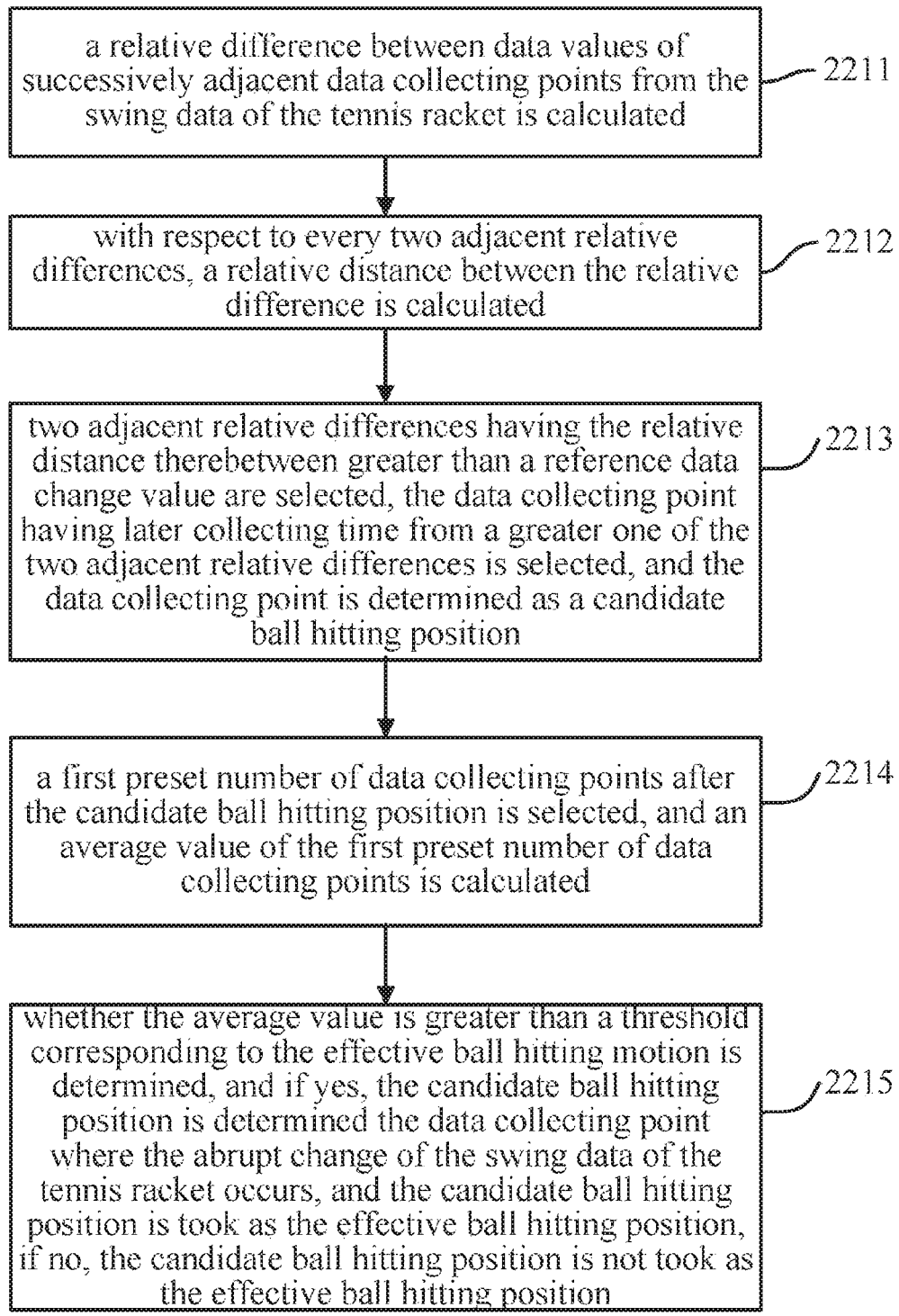
FIG. 4 is a flow chart illustrating a method for a date collecting point where an abrupt change of the swing data of the tennis racket occurs is determined, and the data collecting point is took as the effective ball hitting position according to one embodiment as shown in FIG. 3.

FIG. 4 is a flow chart illustrating a method for a date collecting point where an abrupt change of the swing data of the tennis racket occurs is determined, and the data collecting point is took as the effective ball hitting position according to one embodiment as shown in FIG. 3. In one embodiment, as shown in FIG. 4, Step 221 include the following steps.

In Step 2211, a relative difference between data values of successively adjacent data collecting points from the swing data of the tennis racket is calculated.

In the process of the swing data of the tennis racket collected, among the data collecting point exist time order. Data values of successively adjacent data collecting points are two data collecting points in time order adjacent.

For example, during a process of collecting the swing data of the tennis racket, for a period of time, the collected data points in time order include A1, A2, A3, A4 and A5, respectively acquiring the relative difference between A1 and A2, A2 and A3, A3 and A4, A4 and A5. The relative difference refers to the absolute value of subtraction between data values of successively adjacent data collecting points.

In the Step 2212, with respect to every two adjacent relative differences, a relative distance between the relative difference is calculated.

The relative difference is change in values between data values of successively adjacent data collecting points. Adjacent the relative differences are subtracted and calculated the absolute value to obtain the relative distance. The obtained relative distance and these adjacent differences are establishing correspondences.

For example, during a process of collecting the swing data of the tennis racket; in time order the collected data collecting point is: A1, A2, A3, A4 and A5. In particular, A1=100, A2=120, A3=90, A4=80, A5=120, and then the relative distance B1 between A1 and A2 is 20, the relative distance B2 between A2 and A3 is 30, the relative distance B3 between A3 and A4 is 10, the relative distance B4 between A4 and A5 is 40.

In the Step 2213, two adjacent relative differences having the relative distance therebetween greater than a reference data change value are selected, the data collecting point having later collecting time from a greater one of the two adjacent relative differences is selected, and the data collecting point is determined as a candidate ball hitting position.

The reference data change value is optional configured to 1000.

For example, during a process of collecting the swing data of the tennis racket, in time order, the collected data collecting point is: A1=1000, A2=1800, A3=900, A4=1200 and A5=2400. And then the relative distance B1 between A1 and A2 is 800, the relative distance B2 between A2 and A3 is 900, the relative distance B3 between A3 and A4 is 300, the relative distance B4 between A4 and A5 is 1200. The relative distance B4 is greater than the reference data change value, the relative distance B4 corresponds to A4 and A5, selecting A5 having later collecting time from A4 and A5, A5 is configured as a candidate ball hitting position.

In the Step 2214, a first preset number of data collecting points after the candidate ball hitting position is selected, and an average value of the first preset number of data collecting points is calculated.

The abrupt change corresponding to the candidate ball hitting position, may relate to the ineffective motion, or mistake in a data collecting point and so on. Therefore, need to further verifying the candidate ball hitting position by the swing data of the racket tennis, and determining whether the candidate ball hitting position is the effective ball hitting position, improving the accuracy in selecting the effective ball hitting position.

The first preset number is predefined as the number of the extracted data collecting point. In time sequence, among the candidate ball hitting position and the data collecting points which are having later collecting time and corresponding to the first preset number, extracting all of data collecting point. The first preset number is optional configured to 3.

For the average value of the first preset number of data collecting points, the extracted data collecting point and the candidate ball hitting position have same type of data content, or, the extracted data collecting point and the candidate ball hitting position have different type of data content.

In Step 2215, whether the average value is greater than a threshold corresponding to the effective ball hitting motion is determined, and if yes, the candidate ball hitting position is determined the data collecting point where the abrupt change of the swing data of the tennis racket occurs, and the candidate ball hitting position is took as the effective ball hitting position, if no, the candidate ball hitting position is not took as the effective ball hitting position.

The threshold corresponding to the effective ball hitting motion and the average value of the first preset number of data collecting points correspond to the same type of data content. The threshold corresponding to the effective ball hitting motion is optional configured to 10000.

After the candidate ball hitting position, if the average of the first preset number of data collecting points is greater than the threshold corresponding to the effective ball hitting motion, the average corresponds to the extracted data collecting point; it is indicating that the data segment corresponding to the extracted data collecting point generates great variation, At this point, the great variation is not caused by mistake in collecting, or the ineffective motion.

Through the above process, firstly through data values of successively adjacent data collecting points to determining the candidate ball hitting position, then, in the judgment of the swing data of the tennis racket which is data collecting point of the first preset number backward from the candidate ball hitting position, determining the effective ball hitting position, ensure the accuracy in determining the effective ball hitting position, and finally after extracting the data segment of an effective swing according to the effective ball hitting position, performing implement the recognizing types of swing movements, improving the accuracy in recognizing types of tennis racket movements.

Figure 5:
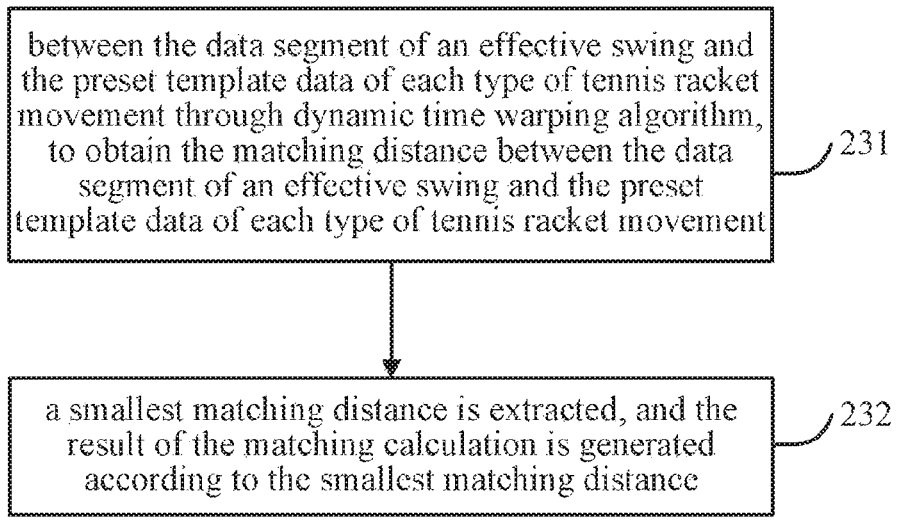
FIG. 5 is a flow chart illustrating a method for between the data segment of an effective swing and preset template data are performed matching calculation, the preset template data corresponding to types of tennis racket movements according to one embodiment as shown in FIG. 2.

FIG. 5 is a flow chart illustrating a method for between the data segment of an effective swing and preset template data are performed matching calculation, the preset template data corresponding to types of tennis racket movements according to one embodiment as shown in FIG. 2. In one embodiment, as shown in FIG. 5, S230 include the following steps.

In step 231, between the data segment of an effective swing and the preset template data of each type of tennis racket movement through dynamic time warping algorithm, to obtain the matching distance between the data segment of an effective swing and the preset template data of each type of tennis racket movement.

The preset template data is the swing data of the tennis racket which is collected for each type of tennis racket movement. In an optional embodiment, all types of tennis racket movements also include the type of the ineffective motion.

Before performing the method for recognizing the swing movement of the tennis racket, the template data is stored in the tennis racket. The template data is the data outputted by the sensor after waving a specified action with the tennis racket, is the data obtained after performing the specified action to complete various types of the swing actions, and then to stored.

In particular, through dynamic time warping algorithm, performing matching calculation between the data segment of an effective swing and the template data of each type of tennis racket movement, to obtain a similarity measure corresponding to the template data of each type of tennis racket movement. According to the highest similarity in all of similarity measures, determining the template data of a type of tennis racket movement, and the type of tennis racket corresponding to the determined template data is the recognition result of the movement of tennis racket.

By dynamic time warping algorithm, to obtain a matching distance which means the similarity measure between the preset template data of each type of tennis racket movement and the data segment of an effective swing. The smaller matching distance, the more similarity between the template data of the type of tennis racket movement and the data segment of an effective swing.

For the any extracted data segment of the effective swing, dynamic time warping algorithm is used matching between the extracted data segment of the effective swing and the template data of each type of tennis racket movement, herein, the preset template data of each type of tennis racket movement is the form of the three-axis gravity components.

In one embodiment, between the data segment of an effective swing and the template data of all type of tennis racket movements, for the template data of each type of tennis racket movement, respectively perform matching calculation on all of forms which are the three-axis gyroscope data, the three-axis accelerated data, and the three-axis resultant force components data, to obtain three matching distances, Finally, the sum of three matching distances is configured to the matching distance.

The detail matching calculation may be implemented with the following detail process:

The template data of a type of tennis racket movement is TemplateData={Template_g, Template_a, Template_v}, herein, the three-axis gyroscope data is Template_g=[gx, gy, gz], the three-axis accelerated data is Template_a=[ax, ay, az], the three-axis resultant force components data by combination thereof generating is Template_v=[vx, vy, vz]. The data segment of an effective swing is TestData={Test_g, Test_a, Test_v}. For the template data of each type of tennis racket movement, respectively performing matching calculation between Test_g and Template_g, Test_a and Template_a, Test_v and Template_v, to obtain the matching distance DTW(Test_g, Template_g), DTW(Test_a, Template_a), DTW(Test_v, Template_v). At this time, between the data segment of an effective swing and the template data of the type of tennis racket movement, the matching distance is Distance=DTW(Test_g, Template_g)+DTW(Test_a, Template_a)+DTW(Test_v, Template_v).

In Step 232, a smallest matching distance is extracted, and the result of the matching calculation is generated according to the smallest matching distance.

The smaller matching distance, the more similarity between the template data of a type of tennis racket movement and the data segment of an effective swing. The type of tennis racket movement corresponding to the template data of the smallest matching distance is the most similarity with the type of tennis racket movement corresponding to the data segment of an effective swing.

In the view of the above, firstly performing matching calculation the data segment of an effective swing and the template data of all types of tennis racket movement, then, acquiring the type of tennis racket movement corresponding to the data segment of an effective swing based on the smallest matching distance from matching calculation, after the data segment of an effective swing extracting, using the template data of each type of tennis racket movement to implement the matching and recognition, the accuracy of recognizing types of swing movements can be improved.

Figure 6:
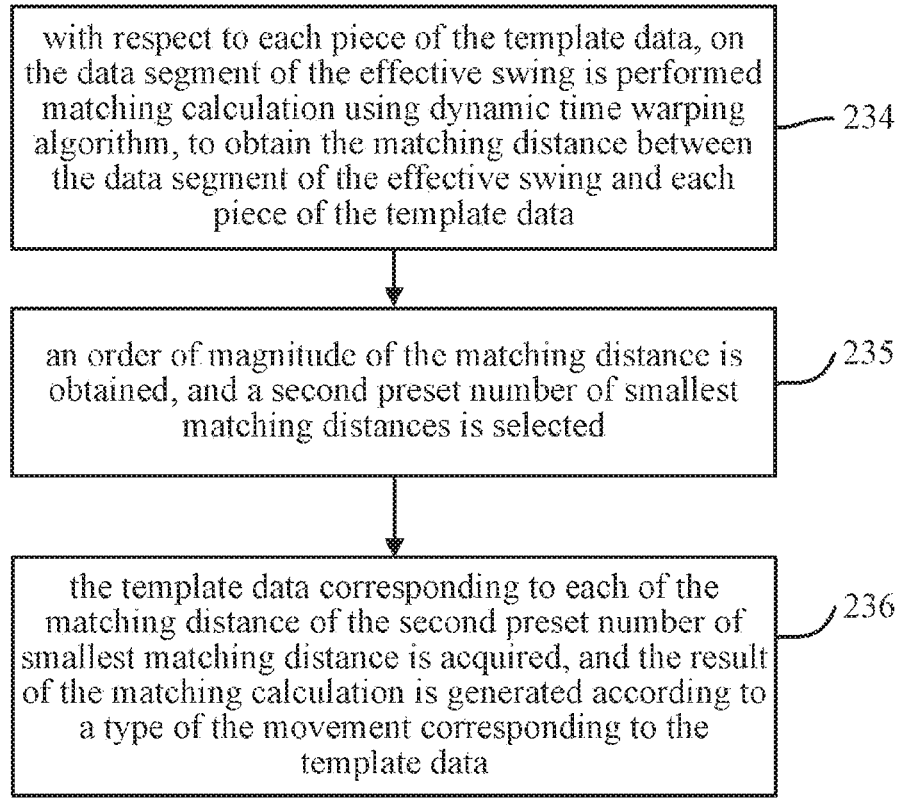
FIG. 6 is a flow chart showing a method for between the data segment of an effective swing and preset template data are performed matching calculation, the preset template data corresponding to types of tennis racket movements according to another embodiment as shown in FIG. 2.

FIG. 6 is a flow chart showing a method for between the data segment of an effective swing and preset template data are performed matching calculation, the preset template data corresponding to types of tennis racket movements according to another embodiment as shown in FIG. 2. In one embodiment, each type of tennis racket movement in the preset template data is provided with a plurality pieces of the template data, as shown in FIG. 6, Step 230 include the following steps.

In Step 234, with respect to each piece of the template data, on the data segment of the effective swing is performed matching calculation using dynamic time warping algorithm, to obtain the matching distance between the data segment of the effective swing and each piece of the template data.

In Step 235, an order of magnitude of the matching distance is obtained, and a second preset number of smallest matching distances is selected.

Where it's understandable that there are a certain difference in similarity measure between the data segment of an effective swing and the template data of each type of tennis racket movement. Therefore, the matching distance corresponding to the data segment of an effective swing is different among pieces of the template data. For the data segment of an effective swing, extracting second preset number of smallest matching distances, to recognize the type of tennis racket movement, avoiding errors in matching calculation of a pieces of the template data to result in identification errors, improve the accuracy in recognizing types of tennis racket movements from the data segment of an effective swing.

For example, the template data of each type of tennis racket movement is M1, M2, M3, M4, M5, M6, M7, M8, M9, M10; the matching distance between the data segment of an effective swing and the template data of each type of tennis racket movement (M1, M2, M3, M4, M5, M6, M7, M8, M9, M10) respectively is 50, 100, 120, 30, 10, 20, 35, 15, 80, 90; the second preset number is configured to 3, in this time, extracting matching distance 10, 20, 15 corresponding to the template data M5, M6, M8.

In Step 236, the template data corresponding to each of the matching distance of the second preset number of smallest matching distance is acquired, and the result of the matching calculation is generated according to a type of the movement corresponding to the template data.

According to the template data corresponding to smaller matching distance, determining the type of tennis racket movement corresponding to the maximum matched times as the result of the matching calculation.

For example, the template data corresponding to several smallest matching distances of the data segment of an effective swing respectively is M5, M6, and M8, the type of tennis racket movement corresponding to M5, M6, and M8 is T1, T1, and T2. So, the type of tennis racket movement corresponding to the data segment of an effective swing is T1.

In one embodiment, if the type of tennis racket movement corresponding to the data segment of an effective swing is the type of the effective motion, in real time output and display the recognition results of movements; if the type of tennis racket movement corresponding to the data segment of an effective swing is the type of ineffective motion, determining the data segment of an effective swing is the data segment of ineffective motion, removing the data segment of ineffective motion.

In an optional embodiment, the second preset number is configured depending on memory size of efficient storage of data, the data size of a piece of the template data and the number of storage type.

In the above process, when each type of tennis racket movement in the preset template data is provided with a plurality pieces of the template data, performing matching calculation on the data segment of an effective swing and each piece of the template data, and then acquiring a second preset number of smallest matching distances, type of tennis racket movement corresponding to the maximum matched times is acquired as the type of tennis racket movement corresponding to the data segment of an effective swing, avoiding calculation errors in matching and mistake in recognizing, the accuracy of recognizing types of tennis racket movements can be improved.

In an optional embodiment, after the Step 240, the method further includes:

According to the data segment of an effective swing, an amount of rotation in a tennis ball and a grade of rotation corresponding to the effective ball hitting position are determined.

In the effective ball hitting position, because the effect of the tennis racket on the tennis ball and relative motions of the tennis racket to the tennis ball, it is present a certain friction between the tennis racket and the tennis ball. This friction causes rotation in the tennis ball. The size of friction is affected by the friction factor $\mu$ between the tennis racket and the tennis ball. The amount of rotation in the tennis ball and the grade of rotation are determined depend on the size of friction, or the angle between the tennis racket performing the effective ball hitting motion and the horizontal plane. Therefore, according to the angle between the tennis racket performing the effective ball hitting motion and the horizontal plane, determining the amount of rotation in the tennis ball and the grade of rotation.

Types of the tennis racket movements include topspin, backspin, volley and overhead i.e. Performing a kinesiology and mechanics analysis of tennis racket movements as following. If a volley being playing, the angle between the tennis racket performing the effective ball hitting motion and the horizontal plane is generally 90°, the variation scope of the angle is 80°~90°; if the topspin or the backspin being playing, the angle between the tennis racket performing the effective ball hitting motion and the horizontal plane in performing the effective ball hitting motion is generally 52.31±7.88°, the variation scope of the angle is 45~60°.

In one embodiment, calculating the amount of rotation in the tennis ball. Specifically, the effective ball hitting position is data collecting point t, data collecting point t is ballScrew-Data=[$g_{tx}$, $g_{ty}$, $g_{tz}$, $a_{tx}$, $a_{ty}$, $a_{tz}$, $v_{tx}$, $v_{ty}$, $v_{tz}$], calculating a resultant force accelerated speed of tennis racket movement about data collecting point t, which is calculated by a formula $a_{t\hat{\imath}} = \sqrt{a_{tx}^2 + a_{ty}^2 + a_{tz}^2}$, the angle between the tennis racket performing the effective ball hitting motion and the horizontal plane is calculated by a formula Theta=arcsin($|a_{tx}|/a_{t\hat{\imath}}$)*180/π.

Further, extracting M consecutive data collecting point backward from data collecting point t, the angle between the tennis racket performing the effective ball hitting motion and the horizontal plane is expressed with $Theta_r$. M is optional configured to 2 or 3.

Calculating the average of $Theta_r$, the average of $Theta_r$ expressed with Aver_Theta, $$\text{Aver\_Theta} = \sum_{i=t}^{t+M} |Theta_i| / M.$$

According to Theta, Aver_Theta and correlation of Theta (correlation ε=|Aver_Theta−Theta|), determining the amount of rotation in the tennis ball and the grade of rotation corresponding to the effective ball hitting motion.

If Theta=90° and ε<7, no rotation in the tennis ball, and the grade of rotation is zero grade of rotation; if 80°<|Theta|<90°, or 0°≤|Theta|<45°, and ε<7, the grade of rotation is referred to the first grade of rotation; if 60°<|Theta|≤80° and ε<7, the grade of rotation is referred to the second grade of rotation: if 45°≤|Theta|<60° and ε<7, the grade of rotation is referred to the third grade of rotation.

Through the established a connection between two tennis rackets, one tennis racket can be received the swing data of the other tennis racket. Recognizing and displaying the type of tennis racket movement and rotation in tennis ball, to determining the type of catching tennis ball motion, the type of catching tennis ball motion is adapted to the type of tennis racket movement and rotation in the tennis ball, offering help for tennis training.

Figure 7:
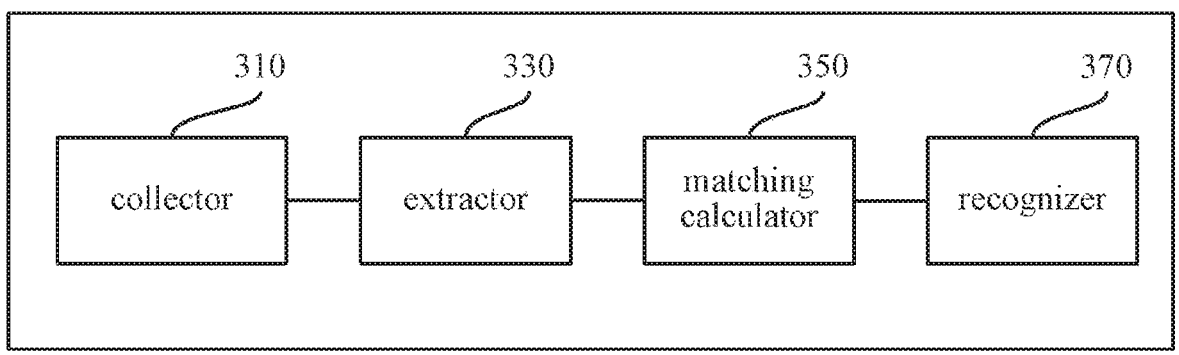
FIG. 7 is a structural block diagram of a device for recognizing movement of a tennis racket according to an exemplary embodiment.

FIG. 7 is a structural block diagram of a device for recognizing movement of a tennis racket according to an exemplary embodiment. As shown in FIG. 7, the device may include a collector 310, an extractor 330, a matching calculator 350 and a recognizer 370.

The collector 310, configured to collect swing data of the tennis racket.

The extractor 330, configured to extract a data segment of an effective swing from the swing data of the tennis racket according to an effective ball hitting position.

The matching calculator 350, configured to perform matching calculation between the data segment of the effective swing and preset template data, the preset template data corresponding to types of tennis racket movements.

The recognizer 370, configured to acquire a recognition result of the movement of tennis racket according to a result of the matching calculation.

In this embodiment, all of function and process relating to every apparatus are illustrated in above methods, which will not repeat here.

Figure 8:
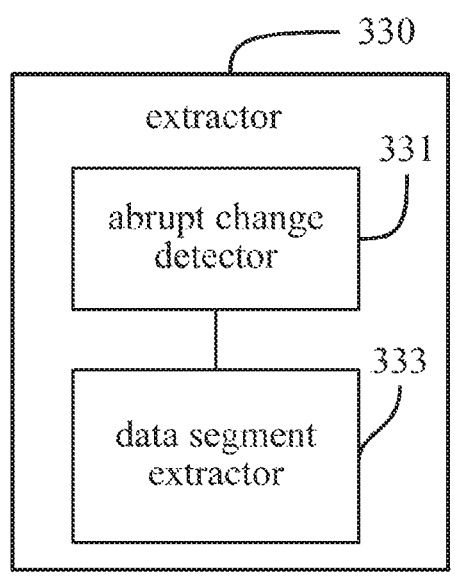
FIG. 8 is a structural block diagram of an extractor in FIG. 7.

Further, FIG. 8 is a structural block diagram of an extractor in FIG. 7. In one embodiment, as shown in FIG. 8, the extractor 330 includes an abrupt change detector 331 and a data segment extractor 333.

The abrupt change detector 331, configured to determine a data collecting point where an abrupt change of the swing data of the tennis racket occurs, and take the data collecting point as the effective ball hitting position.

The data segment extractor 333, configured to extract the data segment of the effective swing from the swing data of the tennis racket according to the effective ball hitting position.

Figure 9:
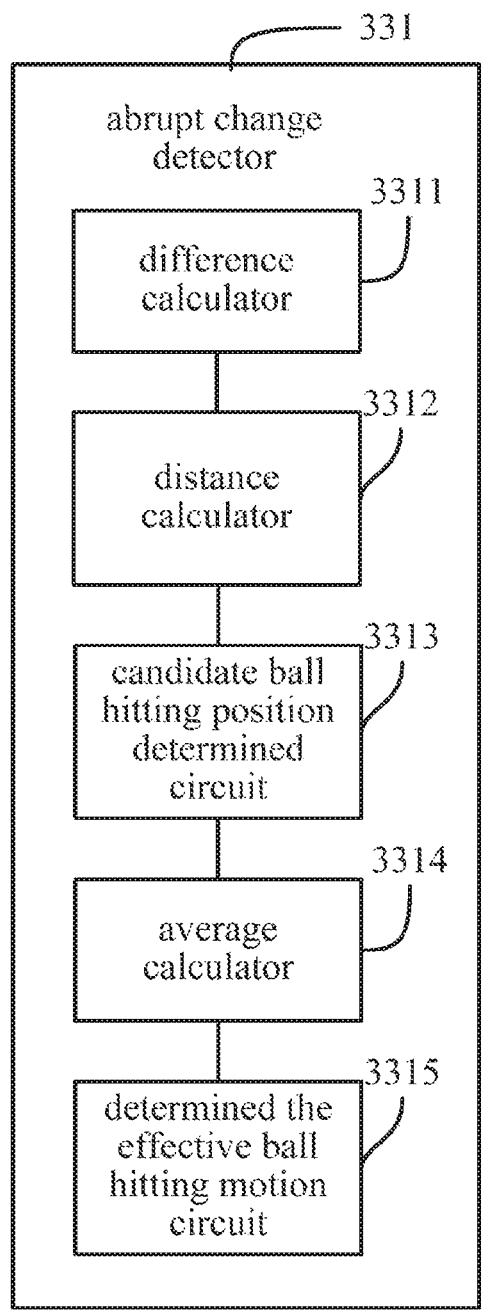
FIG. 9 is a structural block diagram of an abrupt change detector 331 in FIG. 8.

Further, FIG. 9 is a structural block diagram of an abrupt change detector in FIG. 8. In one embodiment, as shown in FIG. 9. The abrupt change detector 331 includes a difference calculator 3311, a distance calculator 3312, a candidate ball hitting position determined circuit 3313, an average calculator 3314 and a determined the effective ball hitting motion circuit 3315.

The difference calculator 3311, configured to calculate a relative difference between data values of successively adjacent data collecting points from the swing data of the tennis racket.

The distance calculator 3312, configured to with respect to every two adjacent relative differences, calculate a relative distance between the relative difference.

The candidate ball hitting position determined circuit 3313, configured to select two adjacent relative differences having the relative distance therebetween greater than a reference data change value, select the data collecting point having later collecting time from a greater one of the two adjacent relative differences, and determine the data collecting point as a candidate ball hitting position.

The average calculator 3314, configured to select a first preset number of data collecting points after the candidate ball hitting position, and calculate an average value of the first preset number of data collecting points.

The determined the effective ball hitting motion circuit 3315, configured to determine whether the average value is greater than a threshold corresponding to an effective ball hitting motion, and if yes, determine that the candidate ball hitting position is the data collecting point where the abrupt change of the swing data of the tennis racket occurs, and take the candidate ball hitting position as the effective ball hitting position.

Figure 10:
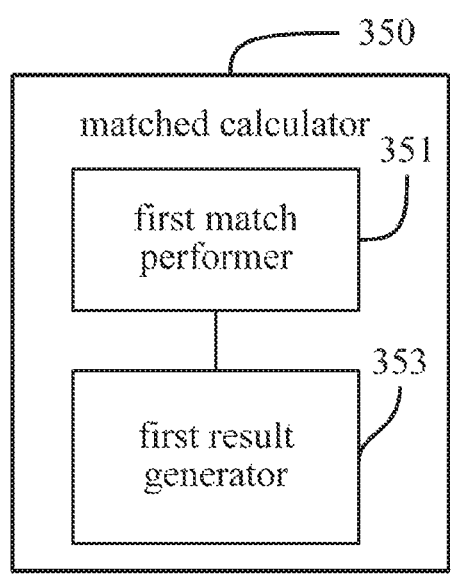
FIG. 10 is a structural block diagram of a matched calculator in FIG. 7.

Further, FIG. 10 is a structural block diagram of a matched calculator in FIG. 7. In one embodiment, as shown in FIG. 10, the matched calculator 350 includes a first match performer 351 and a first result generator 353.

The first match performer 351, configured to perform matching calculation between the data segment of the effective swing and the preset template data of each type of tennis racket movement through dynamic time warping algorithm, to obtain the matching distance between the data segment of the effective swing and the preset template data of each type of tennis racket movement.

The first result generator 353, configured to extract a smallest matching distance, and generate the result of the matching calculation according to the smallest matching distance.

Figure 11:
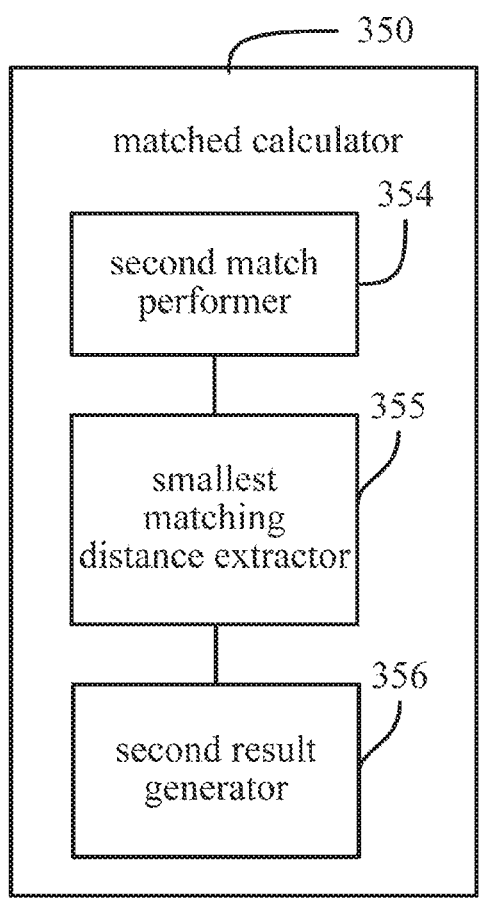
FIG. 11 is a structural block diagram of a matched calculator in FIG. 7.

Further, FIG. 11 is a structural block diagram of a matched calculator in FIG. 7. In one embodiment, as shown in FIG. 11, the matched calculator 350 includes a second match performer 354, a smallest matching distance extractor 355 and a second result generator 356.

The second match performer 354, configured to with respect to each piece of the template data, perform matching calculation on the data segment of the effective swing using dynamic time warping algorithm, to obtain the matching distance between the data segment of the effective swing and each piece of the template data.

The smallest matching distance extractor 355, configured to obtain an order of magnitude of the matching distance, and select a second preset number of smallest matching distances.

The second result generator 356, configured to acquire the template data corresponding to each of the matching distance of the second preset number of smallest matching distance, and generate the result of the matching calculation according to a type of the movement corresponding to the template data.

There is also provided a non-transitory computer readable storage medium storing instructions, executable by a processor of an tracking apparatus, enabling the tracking apparatus to perform a method for recognizing tennis racket movement, including:
  collecting swing data of the tennis racket;
  extracting an data segment of an effective swing from the swing data of the tennis racket according to an effective ball hitting position;
  performing matching calculation between the data segment of the effective swing and preset template data, the preset template data corresponding to types of tennis racket movements; and
  Acquiring a recognition result of the movement of tennis racket according to a result of the matching calculation.

What is claimed is:

1. A method for recognizing movement of a tennis racket, applied to the tennis racket, wherein the tennis racket includes a sensor and an intelligent hardware which includes a processor, wherein the method comprises:
  collecting, by the sensor, swing data of the tennis racket;
  extracting, by the processor, a data segment of an effective swing from the swing data of the tennis racket according to an effective bail hitting position;
  performing, by the processor, matching calculation between the data segment of the effective swing and preset template data, the preset template data corresponding to types of tennis racket movements; and
  acquiring, by the processor, a recognition result of the movement of the tennis racket according to a result of the matching calculation;
  wherein the performing, by the processor, matching calculation between the data segment of the effective swing and preset template data the preset template data corresponding to types of tennis racket movements comprises:
  performing matching calculation between the data segment of the effective swing and the preset template data of each type of tennis racket movement through dynamic time warping algorithm, to obtain a matching distance between the data segment of the effective swing and the preset template data of each type of tennis racket movement; and
  extracting a smallest matching distance, and generating the result of the matching calculation according to the smallest matching distance.

2. The method of claim 1, wherein the extracting, by the processor, the data segment of the effective swing from the swing data of the tennis racket according to an effective ball hitting position comprises:
  determining a data collecting point where an abrupt change of the swing data of the tennis racket occurs, and taking the data collecting point as the effective ball hitting position; and
  extracting the data segment of the effective swing from the swing data of the tennis racket according to the effective ball hitting position.

3. The method of claim 2, wherein the determining, by the processor, the data collecting point where the abrupt change of the swing data of the tennis racket occurs, and taking the data collecting point as the effective ball hitting position comprises:
  calculating a relative difference between data values of successively adjacent data collecting points from the swing data of the tennis racket;
  with respect to every two adjacent relative differences, calculating a relative distance between the relative difference;
  selecting two adjacent relative differences having the relative distance therebetween greater than a reference data change value, selecting the data collecting point having later collecting time from a greater one of the two adjacent relative differences, and determining the data collecting point as a candidate ball hitting position;
  selecting a first preset number of data collecting points after the candidate ball hitting position, and calculating an average value of the first preset number of data collecting points; and
  determining whether the average value is greater than a threshold corresponding to an effective ball hitting motion, and if yes, determining that the candidate ball hitting position is the data collecting point where the abrupt change of the swing data of the tennis racket occurs, and taking the candidate ball hitting position as the effective ball hitting position.

4. The method of claim 1, wherein each type of tennis racket movement in the preset template data is provided with a plurality of pieces of the preset template data, the performing, by the processor, matching calculation between the data segment of the effective swing and preset template data, the preset template data corresponding to types of tennis racket movements comprises:
  with respect to each piece of the template data, performing matching calculation on the data segment of the effective swing using dynamic time warping algorithm, to obtain a matching distance between the data segment of the effective swing and each piece of the template data;
  obtaining an order of magnitude of the matching distance, and selecting a second preset number of smallest matching distances; and
  acquiring the template data corresponding to each of the matching distance of the second preset number of smallest matching distance, and generating the result of the matching calculation according to types of the tennis racket movements corresponding to the template data.

5. A device for recognizing movement of a tennis racket, comprises:
  a processor;
  a sensor; and a memory for storing instructions executable by the processor;

wherein the processor is configured to perform the method, the method comprising:

collecting, by the sensor, swing data of the tennis racket;

extracting, by the processor, a data segment of an effective swing from the swing data of the tennis racket according to an effective ball hitting position;

performing, by the processor, matching calculation between the data segment of the effective swing and preset template data, the preset template data corresponding to types of tennis racket movements; and acquiring, by the processor, a recognition result of the movement of the tennis racket according to a result of the matching calculation;

wherein the performing, by the processor, matching calculation between the data segment of the effective swing and preset template data, the preset template data corresponding to types of tennis racket movements comprises:

performing matching calculation between the data segment of the effective swing and the preset template data of each type of tennis racket movement through dynamic time warping algorithm, to obtain a matching distance between the data segment of the effective swing and the preset template data of each type of tennis racket movement; and extracting a smallest matching distance, and generating the result of the matching calculation according to the smallest matching distance.

6. The device of claim 5, wherein the extracting, by the processor, the data segment of an effective swing from the swing data of the tennis racket comprises:

determining a data collecting point where an abrupt change of the swing data of the tennis racket occurs, and taking the data collecting point as the effective ball hitting position; and extracting the data segment of the effective swing from the swing data of the tennis racket according to the effective ball hitting position.

7. The device of claim 6, wherein the determining, by the processor, the data collecting point where an abrupt change of the swing data of the tennis racket occurs, and take the data collecting point as the effective ball hitting position comprises:

calculating a relative difference between data values of successively adjacent data collecting points from the swing data of the tennis racket;

with respect to every two adjacent relative differences, calculating a relative distance between the relative difference;

selecting two adjacent relative differences having the relative distance therebetween greater than a reference data change value, selecting the data collecting point having later collecting time from a greater one of the two adjacent relative differences, and determining the data collecting point as a candidate ball hitting position;

selecting a first preset number of data collecting points after the candidate ball hitting position, and calculating an average value of the first preset number of data collecting points; and determining whether the average value is greater than a threshold corresponding to an effective ball hitting motion, and if yes, determining that the candidate ball hitting position is the data collecting point where the abrupt change of the swing data of the tennis racket occurs, and taking the candidate ball hitting position as the effective ball hitting position.

8. The device of claim 5, wherein the performing, by the processor, matching calculation between the data segment of the effective swing and preset template data, the preset template data corresponding to types of tennis racket movements comprises:

with respect to each piece of the template data, performing matching calculation on the data segment of the effective swing using dynamic time warping algorithm, to obtain a matching distance between the data segment of the effective swing and each piece of the template data;

obtaining an order of magnitude of the matching distance, and selecting a second preset number of smallest matching distances; and acquiring the template data corresponding to each of the matching distance of the second preset number of smallest matching distance, and generating the result of the matching calculation according to a type of the movement corresponding to the template data.

* * * * *